US00PP29196P2

(12) United States Plant Patent
Hansen

(10) Patent No.: US PP29,196 P2
(45) Date of Patent: Apr. 3, 2018

(54) ×*MANGAVE* PLANT NAMED 'MAN OF STEEL'

(50) Latin Name: ×*Mangave*×*Agave* hybrid
Varietal Denomination: Man of Steel

(71) Applicant: Hans A. Hansen, Zeeland, MI (US)

(72) Inventor: Hans A. Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 15/530,443

(22) Filed: Jan. 13, 2017

(51) Int. Cl.
*A01H 5/00* (2018.01)

(52) U.S. Cl.
USPC ..... Plt./373

(58) Field of Classification Search
USPC ..... Plt./373, 372
CPC ..... A01H 5/12
See application file for complete search history.

*Primary Examiner* — Kent L Bell

(57) ABSTRACT

A new and unique ×*Mangave* plant named 'Man of Steel' characterized by numerous, thin, fibrous, flat, heavily-glaucous, silvery-green leaves with greyed-purple margin and tiny teeth producing a slightly upright habit. Young foliage displays faint wine spotting with exposure to ultraviolet light.

1 Drawing Sheet

Botanical classification: ×*Mangave* times *Agave* hybrid.
Variety denomination: 'Man of Steel'.

BACKGROUND OF THE INVENTION

The present invention relates to the new and distinct ×*Mangave* hybrid plant, ×*Mangave* 'Man of Steel' hybridized by the inventor at a wholesale perennial nursery in Zeeland, Mich., USA as cross between ×*Mangave* 'Bloodspot' (not patented) as the female or seed parent times an unnamed selection of *Agave stricta* (not patented) as the male or pollen parent. The cross was performed in the summer of 2011, seeds were harvested and later sown on Oct. 18, 2011. Through trials at the same nursery the plant was originally assigned the breeder code XMANG-11-06-02. The new plant has been successfully asexually propagated initially by division at the same nursery in Zeeland, Mich. and also by sterile shoot-tip tissue culture. Both methods of asexual propagation systems have been found to produce stable and identical plants that maintain all the unique characteristics of the original plant.

No plants of ×*Mangave* 'Man of Steel' have been sold, under this or any name, in this country or anywhere in the world, prior to the filing of this application, nor has any disclosure of the new plant been made prior to the filing of this application with the exception of that which was disclosed or sold within one year of the filing of this application, and was either derived directly or indirectly from the inventor.

BRIEF SUMMARY OF THE INVENTION

×*Mangave* 'Man of Steel' differs from its parents as well as all other *Manfreda, Agave* and ×*Mangave* known to the applicant. Compared with the male parent *Agave stricta* the new plant has shorter leaves and slightly wider and the young foliage has small spots of very faint wine coloring. Compared with the female parent, 'Bloodspot', the new plant has longer, more fibrous, less brittle, narrower leaves and the foliage coloration is more silvery-green and less burgundy spotting. The most similar cultivars known to the inventor are ×*Mangave* 'Moonglow' U.S. Plant patent application Ser. No. 15/330,178 and ×*Mangave* 'Pineapple Express' U.S. Plant Pat. No. 28,613. Compared with 'Moonglow' the new plant has longer, more arching foliage of more silver-green and less silver-blue, and smaller burgundy spotting. Compared to 'Pineapple Express' the new plant has longer, narrower and more arching foliage with more silver-green coloration with heavier glaucous coating and less burgundy spotting in the leaves.

The new plant, 'Man of Steel', is unique from all of the above cultivars and all *Agave,* ×*Mangave* and *Manfreda* known to the inventor by the following combined traits:

1. Numerous, thin, fibrous, flat, silvery-green leaves projecting outward to slightly upwardly in a tight habit;
2. Foliage develops heavy glaucous covering and thin greyed-purple margin with tiny teeth;
3. Young foliage displays small, faint wine spotting on both surfaces with exposure to ultraviolet light;
4. Leaves have a long, firm, burnt orange-colored apical spine that darkens with maturity;
5. Moderate growth rate.

BRIEF DESCRIPTION OF THE DRAWINGS

The photographs of ×*Mangave* 'Man of Steel'; demonstrate the overall appearance of the new plant including the unique traits. The colors are as accurate as reasonably possible with color reproductions. Ambient light spectrum, temperature, source and direction may cause the appearance of minor variation in color.

DETAILED BOTANICAL DESCRIPTION

Figure 1:
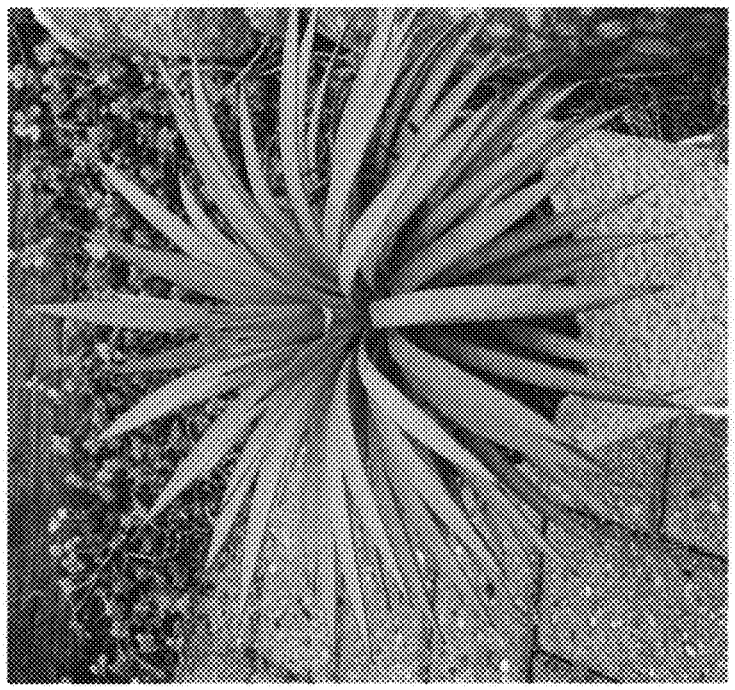
FIG. 1 shows the habit of a four-year-old plant grown in a greenhouse in Zeeland, Mich.
Figure 2:
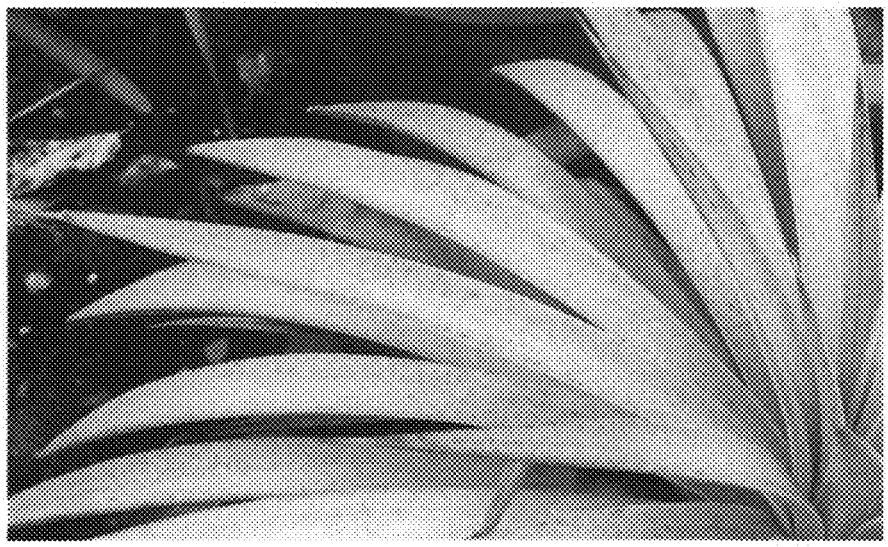
FIG. 2 shows a close-up of foliage of a two-year-old plant grown outdoors in Raleigh, N.C., with ultraviolet light exposure.

The following descriptions and color references are based on the 2001 edition of The Royal Horticultural Society Colour Chart except where common dictionary terms are used. The new plant, ×*Mangave* 'Man of Steel', has not been observed under all possible environments. The phenotype may vary slightly with different environmental conditions, such as temperature, light, fertility, moisture and maturity levels, but without any change in the genotype. The following observations and size descriptions are of a five-year-old plant in a commercial wholesale greenhouse in Zeeland, Mich. with supplemental water and fertilizer as needed.

Parentage: 'Bloodspot' as female (seed) parent and an unnamed *Agave stricta* as the male (pollen) parent;

Propagation: Division of side shoots and sterile shoot-tip tissue culture;

Time to initiate roots from tissue culture: About 21 days;

Growth rate: Moderate;

Crop time: About 12 to 14 weeks to finish in a 3.8 liter container from a 35 mm tissue culture growing at about 21° C.;

Rooting habit: Fleshy, lightly branching, with roots up to 15 cm long;

Root color: Nearest RHS 158D;

Plant shape and habit: Succulent, herbaceous, freeze-tender perennial with basal rosettes of about 160 leaves radially emerging and outwardly and slightly arching from central stem extending below the base of the plant when grown in containers, producing a radially-symmetrical, slightly upright mound.

Plant size: Foliage height about 50.0 cm tall from soil line to the top of the leaves and about 35.0 cm wide at the widest point slightly below soil line in container;

Foliage description: Gladiate; simple; margins finely dentate with flexible teeth, teeth about 0.5 mm long and spaced about 1.0 mm apart; apex spinose; base truncate, sessile, clasping; flat; bi-laterally symmetrical; younger foliage with small wine-colored spots to about 1.6 cm long and 1.3 cm across;

Leaf size: To about 22.0 cm long, about 1.5 cm wide at base and 3.0 mm thick, average about 20.5 cm long, 1.5 cm wide and 2.5 mm thick; spots to about 1.0 mm diameter;

Foliage fragrance: None observed;

Leaf blade color:

*Adaxial* (*young*).—Between RHS N138D and RHS 188B with spots nearest RHS N187B.

*Abaxial* (*young*).—Between RHS N138D and RHS 188B with spots nearest RHS N187B.

*Adaxial* (*mature*).—Nearest RHS 191A; Abaxial (mature): blend between RHS 144A and RHS 138A; adaxial and abaxial margin of less than 1.0 mm wide nearest RHS 187A.

*Teeth*.—Less than 0.5 mm long; flexible; about 13 teeth per centimeter on young leaves and about 8 teeth per centimeter on mature leaves; color nearest RHS 187A.

Spine: Sharp and hard; emarginate; average about 1.6 cm long and about 2.0 mm wide at base;

Spine color: Young leaves nearest RHS N170A, maturing to between RHS 175A and RHS 176A;

Petiole: Sessile;

Veins: Parallel; not distinct abaxial or adaxial;

Stem: Terete; covered with leaves; about 3.5 cm across and extending to about 5.0 cm above soil; without branching, attitude upwards, erect;

Flowers have not yet been observed;

Fruit and seed have not yet been observed;

Disease resistance: ×*Mangave* 'Man of Steel' has not been observed to be resistant to diseases beyond that which is normal for ×*Mangave, Agave* or *Manfreda*. The plant is xeromorphic and survives well with minimal water once established. The new plant is hardy at least from USDA zone 9a to 10. Full extent of winter hardiness has not been tested.

It is claimed:

1. A new and distinct cultivar of ornamental ×*Mangave* plant named 'Man of Steel' as herein described and illustrated, suitable for the garden or as a potted plant in the garden or home.

* * * * *